(12) United States Patent
Boutillette et al.

(10) Patent No.: US 7,264,001 B2
(45) Date of Patent: Sep. 4, 2007

(54) GUIDEWIRE EXIT TOOL

(75) Inventors: Michael P. Boutillette, Waltham, MA (US); M. Kevin Richardson, Hopkinton, MA (US)

(73) Assignee: SCIMED Life Systems, Inc., Maple Grove, MN (US)

( * ) Notice: Subject to any disclaimer, the term of this patent is extended or adjusted under 35 U.S.C. 154(b) by 256 days.

(21) Appl. No.: 10/601,075

(22) Filed: Jun. 20, 2003

(65) Prior Publication Data

US 2004/0260205 A1 Dec. 23, 2004

(51) Int. Cl.
*A61B 19/00* (2006.01)

(52) U.S. Cl. .................. 128/898; 604/103.04

(58) Field of Classification Search ........... 604/103.04, 604/164.05, 160, 161, 524, 500; 128/898
See application file for complete search history.

(56) References Cited

U.S. PATENT DOCUMENTS

| | | | | |
|---|---|---|---|---|
| 2,552,450 A * | 5/1951 | Paoli | ............... | 452/3 |
| 3,101,727 A * | 8/1963 | Wiseman | .............. | 132/329 |
| 3,584,625 A * | 6/1971 | Swick | ............... | 604/161 |
| 3,610,239 A * | 10/1971 | Huggins | ............... | 604/161 |
| 3,831,274 A * | 8/1974 | Horrocks | ............... | 30/90.4 |
| 3,877,429 A * | 4/1975 | Rasumoff | ............... | 604/158 |
| 4,054,136 A * | 10/1977 | von Zeppelin | ............ | 604/160 |
| 4,858,810 A | 8/1989 | Intlekofer et al. | | |
| 5,314,408 A | 5/1994 | Salmon et al. | | |
| 5,322,513 A * | 6/1994 | Walker | ............... | 604/161 |
| 5,364,376 A * | 11/1994 | Horzewski et al. | ......... | 604/528 |
| 5,437,074 A * | 8/1995 | White et al. | ................. | 15/105 |
| 5,458,584 A * | 10/1995 | Ginn et al. | ............... | 604/528 |
| 5,460,185 A * | 10/1995 | Johnson et al. | ............. | 600/585 |
| 5,755,685 A * | 5/1998 | Andersen | .............. | 604/509 |
| 5,755,695 A | 5/1998 | Erickson et al. | | |
| 5,830,191 A | 11/1998 | Hildwein et al. | | |
| 6,132,390 A | 10/2000 | Cookston et al. | | |
| 6,159,198 A * | 12/2000 | Gardeski et al. | ............ | 604/523 |
| 6,165,167 A * | 12/2000 | Delaloye | .............. | 604/528 |
| 6,485,466 B2 * | 11/2002 | Hamilton | .............. | 604/158 |
| 6,497,681 B1 * | 12/2002 | Brenner | ................. | 64/164.05 |
| 6,723,071 B2 * | 4/2004 | Gerdts et al. | ........... | 604/103.04 |
| 6,879,854 B2 * | 4/2005 | Windheuser et al. | ....... | 600/434 |
| 2003/0233043 A1* | 12/2003 | Windheuser et al. | ....... | 600/434 |

FOREIGN PATENT DOCUMENTS

| | | |
|---|---|---|
| DE | 100 42 424 A1 | 3/2002 |
| WO | 99/37212 | 7/1999 |
| WO | 02/078776 A2 | 10/2002 |

* cited by examiner

*Primary Examiner*—Nicholas Lucchesi
*Assistant Examiner*—Theodore J. Stigell
(74) *Attorney, Agent, or Firm*—Christensen O'Connor Johnson Kindness PLLC

(57) ABSTRACT

A guidewire exit tool includes a pin that is insertable into a guidewire channel of a rapid exchange-type catheter. The pin has at least one tapered end that urges a guidewire out of a slit in guidewire channel. In one embodiment the exit tool has an oval handle that is angled with respect to the longitudinal axis of the pin such that the tool can be easily grasped and moved along the guidewire channel.

4 Claims, 4 Drawing Sheets

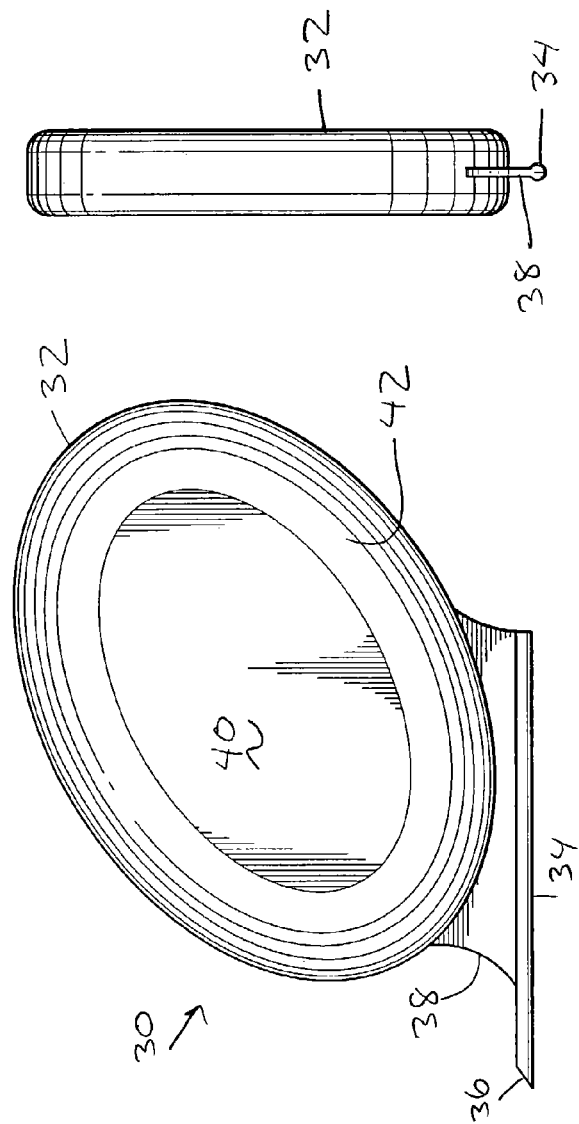

GUIDEWIRE EXIT TOOL

FIELD OF THE INVENTION

The present invention relates to medical devices in general, and in particular to rapid exchange-type catheters.

BACKGROUND OF THE INVENTION

As an alternative to invasive-type surgeries whereby a physician creates an incision to access a desired location in the patient's body, many minimally invasive surgeries and in vivo examinations are being performed using catheters that are inserted into a patient's body. With a catheter in place, medical devices are routed through a lumen in the catheter in order to obtain tissue samples, perform a surgical procedure or diagnose tissue in a patient's body.

To insert a catheter, many physicians first use a guidewire that is routed to a desired location in the patient's body. The guidewire then acts as a rail over which catheters or other medical devices can be easily routed to the desired location.

FIG. 1 illustrates a conventional guidewire and rapid exchange-type catheter. A catheter 10 includes a working lumen 12 through which a medical device can be inserted, and a guidewire lumen 14 through which a guidewire 18 is passed. The catheter 10 can be threaded over the guidewire 18 by inserting the proximal end of the guidewire into the distal end of the guidewire lumen 14. Alternatively, the distal end of the guidewire 18 can be inserted into the proximal end of the lumen 14 by threading it through an introducer 20 at the proximal end of the catheter. The introducer 20 acts as a funnel to guide the distal tip of the guidewire into the guidewire lumen 14.

In some instances, it is desirable to exchange the catheter 10 for another catheter while leaving the guidewire 18 in place. In order to avoid removing the guidewire 18, the proximal end of the guidewire is held stationary while the catheter 10 is removed. If a conventional catheter is used, the guidewire must be substantially longer than the catheter, in order to pull the catheter off the guidewire. Such long guidewires may be unwieldy in the operating room.

To reduce the need for such long guidewires, many catheters include a rapid exchange-type feature whereby the majority of guidewire lumen 14 is formed as a channel 16 having a slit that extends along a length of the catheter 10. The catheter can be removed from the guidewire by pulling the guidewire through the slit in channel 16 up to the point where the channel becomes an enclosed lumen towards the distal end of the catheter. The remaining distal section of the guidewire lumen can then be pulled over the proximal end of the guidewire. Rapid exchange-type catheters and their use are considered to be well known to those of ordinary skill in the medical device arts.

In order to remove a guidewire from a rapid exchange-type catheter when backloading, the proximal end of the guidewire is forced through the slit in guidewire channel 16. This is typically accomplished by bending the catheter 10 in the region of the proximal end of the guidewire such that the proximal tip pokes through the slit in the channel 16. Many modern guidewires include tips of differing flexibilities at their proximal and distal ends, thereby giving the physician the option of adjusting the flexibility depending on which end of the guidewire is inserted into the patient. However, such flexible tips are difficult to use with rapid exchange-type catheters because they are not stiff enough to be forced through the slit in the channel 16 without severely bending and possibly kinking the catheter. Therefore, there is a need for a technique to use rapid exchange-type catheters with guidewires having flexible proximal ends.

SUMMARY OF THE INVENTION

To address the problems discussed above, the present invention is a tool for urging a guidewire out of a guidewire channel of a rapid exchange-type catheter. The tool includes a handle and a pin that fits within the guidewire channel. One end of the pin may be tapered to engage and lift the proximal end of a guidewire out of a slot in the guidewire channel.

In one exemplary embodiment of the invention, the handle is an oval disk having a center depression and an annular ring around the perimeter of the disk. The oval has a major axis that is angled with respect to the longitudinal axis of the pin.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 4 is a side elevational view of a guidewire exit tool in accordance with one embodiment of the present invention;

FIG. 5 is a rear elevational view of a guidewire exit tool in accordance with one embodiment of the present invention;

FIG. 6 is a front elevational view of a guidewire exit tool in accordance with one embodiment of the present invention;

FIG. 7 is a top plan view of a guidewire exit tool in accordance with one embodiment of the present invention; and FIG. 8 is a bottom view of a guidewire exit tool in accordance with one embodiment of the present invention.

DETAILED DESCRIPTION OF THE PREFERRED EMBODIMENT

Figure 1:
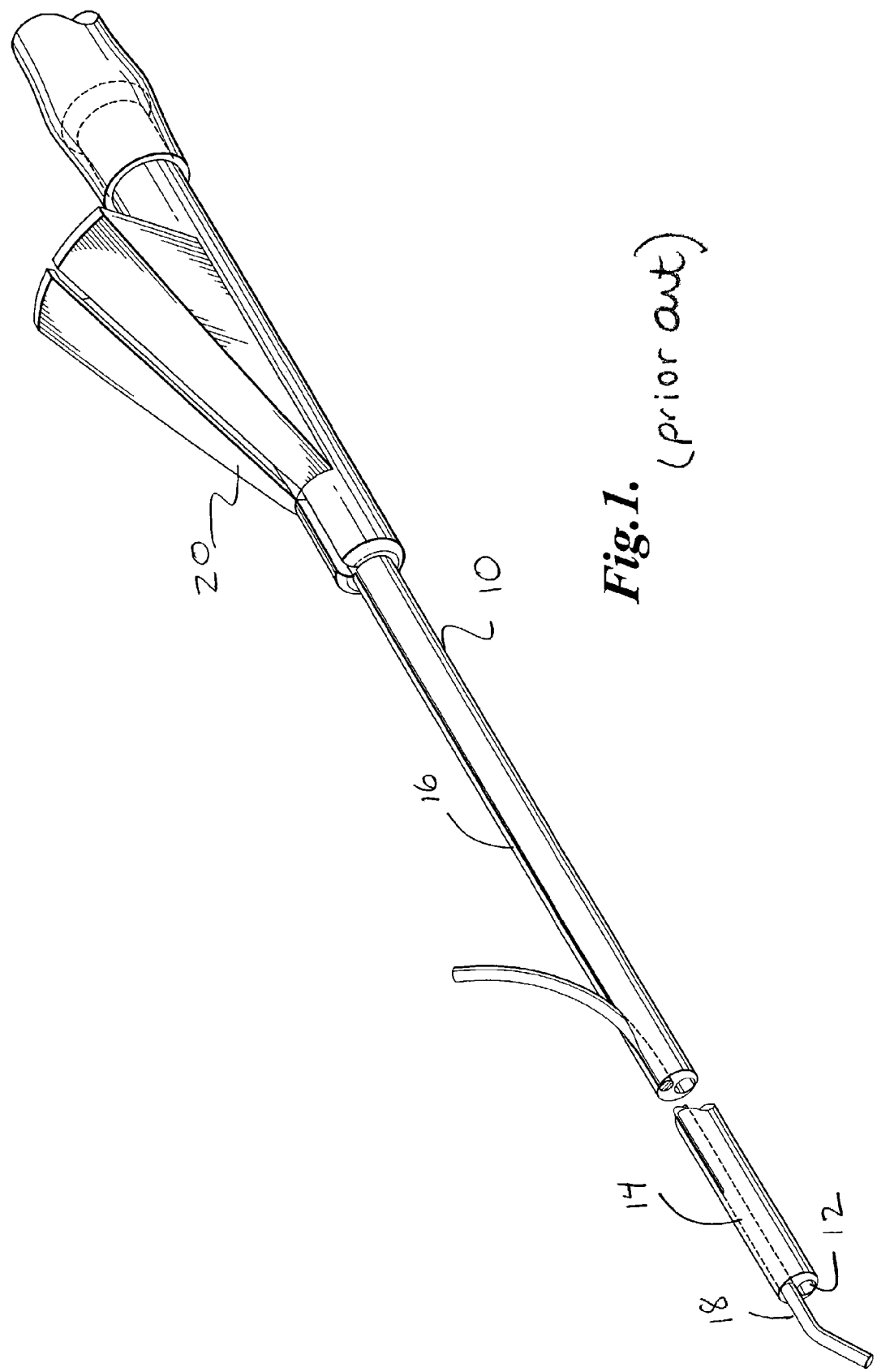
FIG. 1 illustrates a conventional rapid exchange-type catheter and guidewire.
Figure 2:
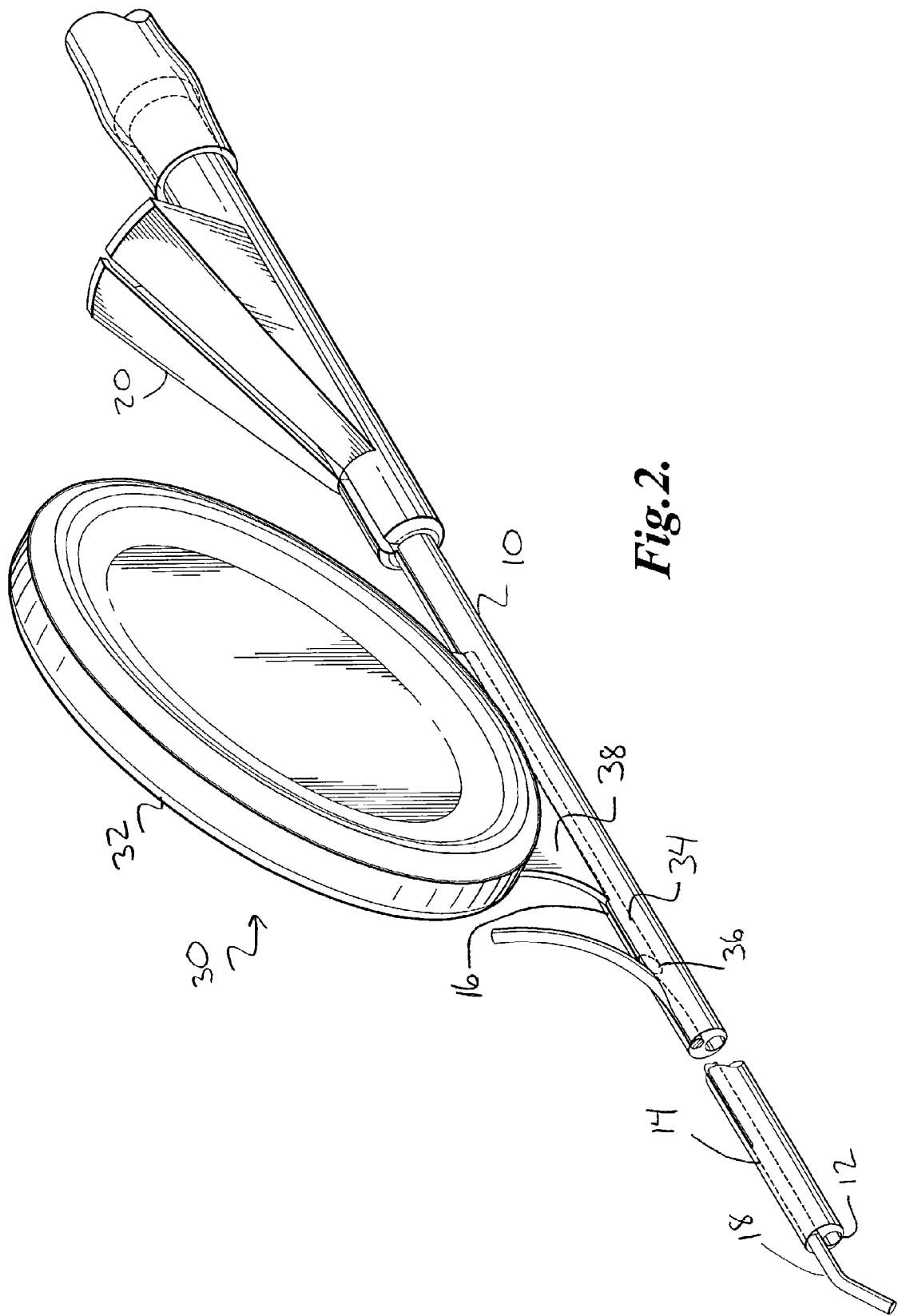
FIG. 2 illustrates a catheter and a guidewire exit tool in accordance with one embodiment of the present invention.
Figure 3:
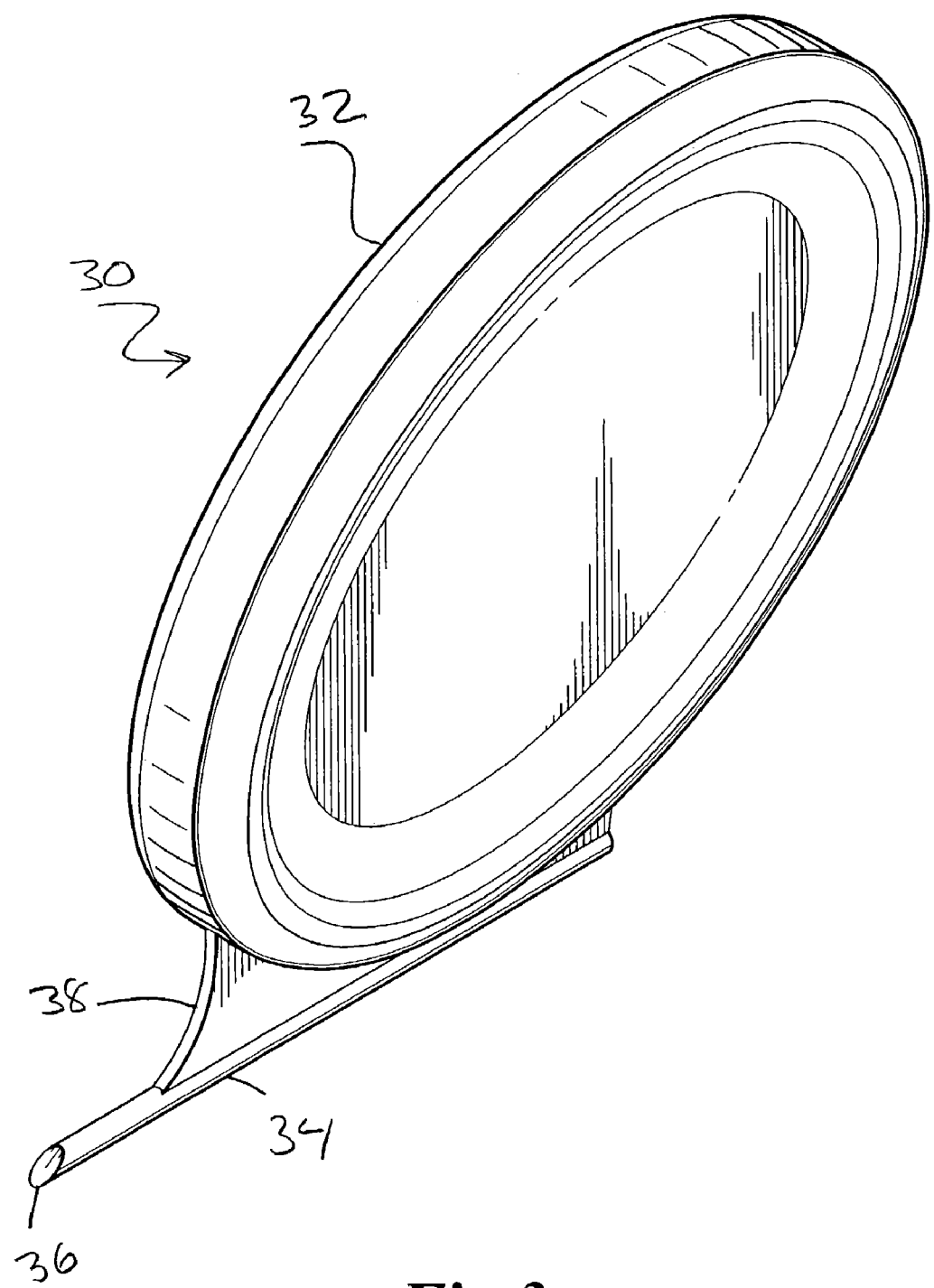
FIG. 3 is an isometric view of a guidewire exit tool in accordance with one embodiment of the present invention.

As best shown in FIG. 3, the present invention is a guidewire exit tool 30 that aids in retrieving the proximal end of a guidewire from a guidewire channel in a rapid exchange-type catheter. The guidewire exit tool has a handle 32 for grasping the tool and a pin 34 that is insertable into the guidewire channel 16. The pin 34 is secured to the handle 32 by a web or "rib" 38. One end of the pin 34 may include a tapered point 36. As shown in FIG. 2, the diameter of the pin 34 is selected to fit within the guidewire channel 16 but is larger than the width of the slit in the channel 16. Movement of the pin 34 with respect to the proximal end of the guidewire 18 causes the tapered point 36 to engage the proximal end of the guidewire 18 and lift it out of the channel 16 so that it can be grasped by a physician. The guidewire exit tool 30 can be moved against the guidewire 18 or the guidewire 18 can be moved against the guidewire exit tool 30 in order to push the proximal end of the guidewire through the slit in the channel 16.

FIG. 4 is a side elevational view of one design of a guidewire exit tool according to the present invention. In this design, the handle 32 comprises an oval disk having a central depression 40 on either side of the disk and a raised annular ring 42 around the perimeter of the handle. The major axis of the oval disk is oriented at approximately 30° to the longitudinal axis of the pin 34. The orientation of the disk and depressions within the handle 32 form an ergonomic grip that is easily grasped by the thumb and forefinger of a user for movement within a guidewire channel. The other side of the guidewire exit tool is the same as shown in FIG. 4.

The guidewire exit tool 30 can be injection molded of thermoplastic or other materials.

FIG. 5 is a rear elevational view of the design of the guidewire exit tool 30, and FIG. 6 is a front elevational view of the design of the guidewire exit tool 30.

As shown in FIG. 6, the pin 34 has a diameter that is slightly wider than the diameter of the flexible web 38 that holds the pin 34 to the handle 32. The width of the web 38 is designed to fit through a slit in the channel 16 of the catheter 10. The diameter of the pin 34 is slightly wider than the slit in the channel 16 such that the guidewire exit tool cannot be easily pulled out of the guidewire channel through the slit.

FIG. 7 is a top plan view of the design of the guidewire exit tool in accordance with the present invention, and FIG. 8 is a bottom plan view of the design of the guidewire exit tool according to the present invention.

While the preferred embodiment of the invention has been illustrated and described, it will be appreciated that various changes can be made therein without departing from the scope of the invention. For example, a guidewire exit tool could have a conventional handle or a handle with a differently shaped ergonomic grip. It is therefore intended that the scope of the invention be determined from the following claims and equivalents thereof.

The invention claimed is:

1. A method of using a guidewire with a rapid exchange-type catheter having a guidewire channel and a slot in a wall along a length of the guidewire channel, comprising:
   (a) loading a guidewire into the guidewire channel of the rapid exchange-type catheter;
   (b) engaging a proximal end of the guidewire with a guidewire exit tool, the guidewire exit tool including:
      (i) a handle;
      (ii) a pin secured to the handle, the pin having a forward facing surface that is solid in the center and tapered; and
      (iii) a web that secures the pin to the handle, the web being positioned laterally with respect to the long axis of the pin, the web having a forward facing surface that is substantially blunt to prevent cutting the catheter; and
   (c) wherein the guidewire exit tool is positioned so that the pin is in the guidewire channel and the web extends through the slot and the tapered forward facing surface of the pin faces the slot to lift the guidewire out of the guidewire channel through the slot.

2. The method of claim 1, wherein the proximal end of the guidewire engages with the guidewire exit tool by sliding the guidewire exit tool in the guidewire channel.

3. The method of claim 1, wherein the proximal end of the guidewire engages with the guidewire exit tool by sliding the guidewire against the guidewire exit tool.

4. A method of using a guidewire with a rapid exchange-type catheter having a guidewire channel and a slot in a wall along a length of the guidewire channel, comprising:
   (a) loading a guidewire into the guidewire channel of the rapid exchange-type catheter;
   (b) engaging a proximal end of the guidewire with a guidewire exit tool, the guidewire exit tool including:
      (i) a pin that is generally cylindrical and has a tapered distal end, wherein the tapered distal end is solid in the center;
      (ii) a handle; and
      (iii) a web that secures the pin to the handle, the web being attached to the pin laterally with respect to the long axis of the pin; and
   (c) wherein the guidewire exit tool is positioned so that the pin is in the guidewire channel and the web extends through the slot and the tapered distal end of the pin faces the slot at an angle to lift the guidewire out of the guidewire channel through the slot.

* * * * *